US006553250B2

(12) United States Patent
Rantala (10) Patent No.: US 6,553,250 B2
(45) Date of Patent: Apr. 22, 2003

(54) SYSTEM FOR ECG MONITORING WITH SELECTIVE LEAD SWITCHING

(75) Inventor: Börje Rantala, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 84 days.

(21) Appl. No.: 09/786,829

(22) Filed: Mar. 9, 2001

(65) Prior Publication Data

US 2002/0138011 A1 Sep. 26, 2002

Related U.S. Application Data

(63) Continuation-in-part of application No. PCT/FI00/00617, filed on Jul. 5, 2000.

(30) Foreign Application Priority Data

Jul. 8, 1999 (FI) .................................................. 991571

(51) Int. Cl.⁷ ............................................ A61B 5/0432
(52) U.S. Cl. ...................................... 600/509; 600/522
(58) Field of Search ................................ 600/509, 522, 600/523; 128/908

(56) References Cited

U.S. PATENT DOCUMENTS 4,243,046 A * 1/1981 Weinstein et al. .......... 600/522
4,341,225 A * 7/1982 Gallant et al. ............. 128/902
4,696,527 A    9/1987 Ding et al.
5,341,812 A    8/1994 Allaire et al.

FOREIGN PATENT DOCUMENTS

| EP | 835635 | 4/1998 |
| WO | 96/14016 | 5/1996 |
| WO | 97/14358 | 4/1997 |

* cited by examiner

Primary Examiner—Kennedy Schaetzle
(74) Attorney, Agent, or Firm—Andrus, Sceales, Starke & Sawall, LLP (57) ABSTRACT

The invention concerns a system for ECG monitoring, comprising measuring electrodes R, F, L, N; $V_1$, $V_2$, $V_3$, $V_4$, $V_5$, $V_6$) attached to a patient (P) in accordance with a standard electrode placement; signal leads (1–10) connected to corresponding measuring electrodes (R, F, L, N; $V_1$, $V_2$, $V_3$, $V_4$, $V_5$, $V_6$) each of said signal leads being provided with a first connector element (11); a collecting connector (13) containing second connector elements (14) for receiving the first connector elements (11); an ECG apparatus comprising an amplifier unit (16) to which the measurement signals are passed from the collecting connector; and change-over switches (18–22) which are so implemented that, in a first connection position (I), they will conduct the measurement signals from the measuring electrodes (R, F, L, N; $V_1$, $V_2$, $V_3V_4$, $V_5$, $V_6$) attached to the patient (P) to the ECG apparatus so that the corresponding signal leads (1–10) are connected to a patient, while in a second connection position (II) they establish a shielding ground connection for at least some of said signal leads.

22 Claims, 6 Drawing Sheets

SYSTEM FOR ECG MONITORING WITH SELECTIVE LEAD SWITCHING

CROSS REFERENCE TO RELATED APPLICATION

The present U.S. national stage application claims the priority of International Application PCT/FI00/00617 filed Jul. 5, 2000, which international application was published on Feb. 1, 2000 as International Publication WO 01/06923 A1 in the English language. The International Application claims the priority of Finnish Patent Application 991571, filed Jul. 8, 1999.

The present application is a continuation-in-part of International Application PCT/FI00/00617, filed Jul. 5, 2000.

The present invention relates to a system as defined in the preamble of claim 1.

Figure 1:
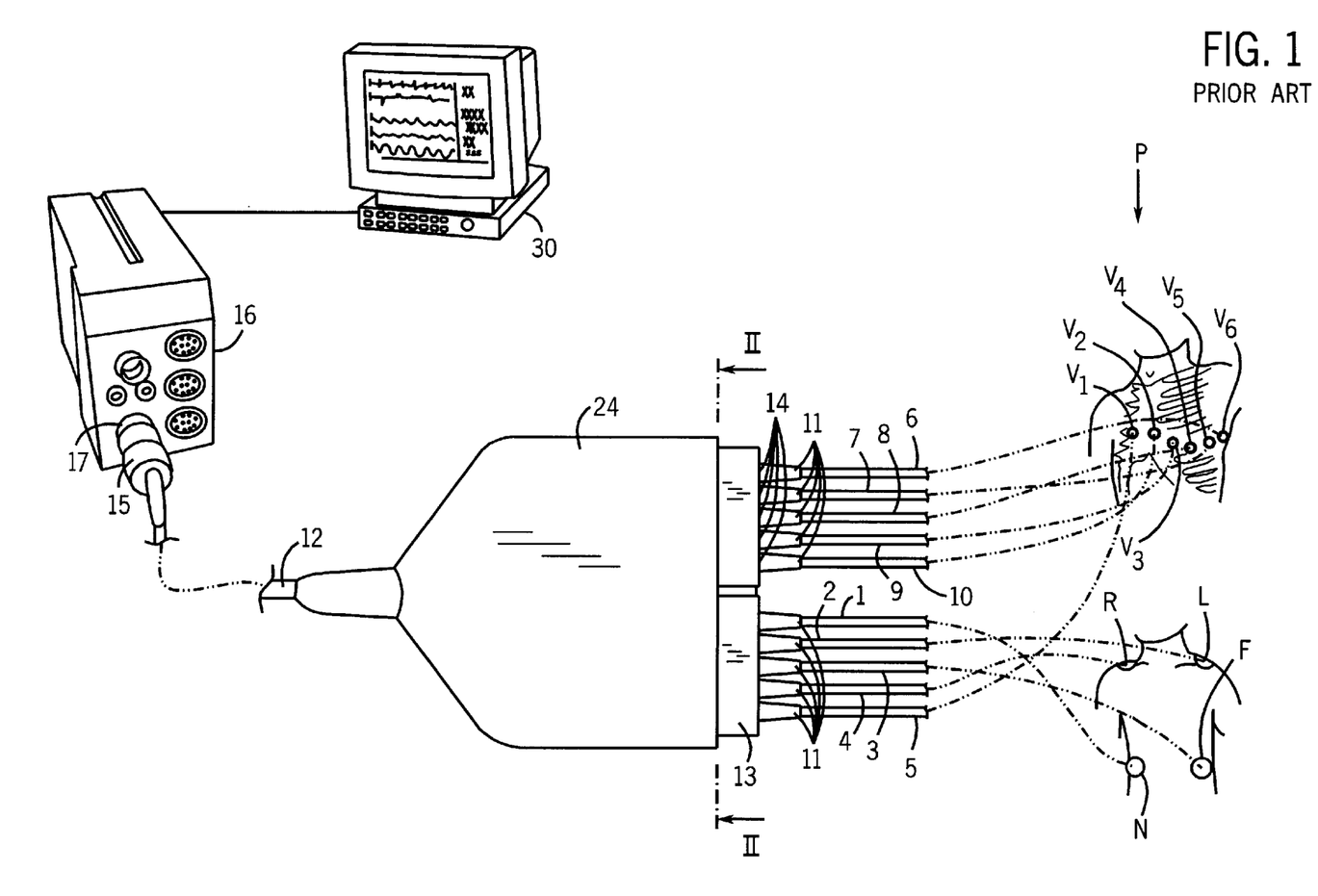
FIG. 1 is a diagrammatic representation of prior-art system.
Figure 2:
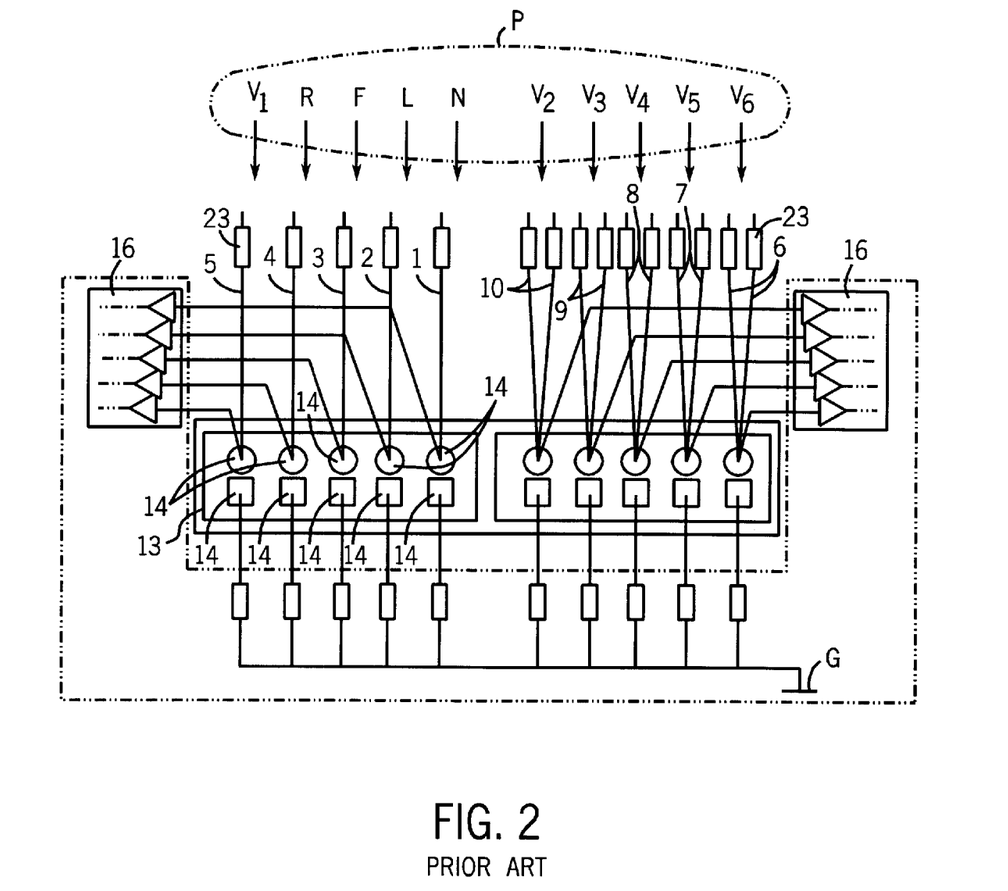
FIG. 2 is a diagrammatic representation of prior-art collecting connector as seen from direction II—II in FIG. 1, and a diagram of the prior-art system.

In the prior art, a system for ECG monitoring as represented by the diagrams in FIGS. 1 and 2 is known. In FIG. 1, the same patient P is diagrammatically represented by two pictures of the torso, where the lower picture shows a standard four-point placement of measuring electrodes R, F, L and N (so-called limb electrodes). For the sake of clarity, the upper picture separately shows a standard placement of ECG measuring electrodes, i.e. precordial electrodes $V_1$, $V_2$, $V_3$, $V_4$, $V_5$, $V_6$ on the patient's thorax. Together the limb electrodes and precordial electrodes form a so-called 12-lead connection system. A so-called 5-lead connection system also used in ECG measurement consists of limb electrodes together with one of the precordial electrodes, e.g. R, F, L, N and $V_1$.

A 12-lead connection system as presented in FIGS. 1 and 2 comprises 1–10 signal leads, which are connected to corresponding measuring electrodes R, L, N, F; $V_1$, $V_2$, $V_3$, $V_4$, $V_5$, $V_6$ as mentioned above, attached to the patient P according to standard electrode placement Each signal lead 1–10 is provided with a first connector element 11. The system further comprises a collecting cable 12 with an adapter 24 at its end. The adapter 24 comprises a collecting connector 13 provided with second connector elements 14 for receiving the first connector elements 11 of the signal lead. At the other end of the cable 12 is a third connector element 15 The system further comprises an ECG apparatus 30, which comprises an amplifier unit 16.

The amplifier unit 16 is provided with a fourth connector element 17, to which the third connector element 15 of the collecting cable 12 is connected.

ECG monitoring and diagnostic so-called 12-lead ECG have traditionally been performed using different sets of equipment. Monitoring was performed as a continuous process using 3-lead or 5-lead equipment and 12-lead monitoring was generally performed when necessary under the supervision of a cardiologist as a short separate operation. However, it is possible to build an apparatus using modern electronics which brings the price of 12-lead ECG to a reasonable level, thus making it sensible to use continuous 12-lead monitoring. However, 12-lead equipment is more complicated than 5-lead equipment as it needs ten measuring electrodes as Mentioned above: R, F, L, N,; $V_1$, $V_2$, $V_3$, $V_4$, $V_5$, $V_6$ and therefore also ten patient cables, i.e. signal leads 1–10 from the amplifier to the patient's skin. The end of the shielded collecting cable 12 in the prior-art 12-lead system is overloaded with a collecting connector 13, which is also presented in FIG. 2 as a diagram showing it in an end view. It comprises twenty connector elements 14 in all. Placed in the upper row on the right are circular connector elements 14 for the connector elements.11 of the signal leads 1–5 coming from the limb electrodes R, F, L, N, and one precordial electrode $V_1$. Connected to the circular connector elements $14_1$ in the left-hand part of the upper row are the connector elements 11 of the signal leads 6–10 coming from the precordial electrodes $V_2$, $V_3$, $V_4$, $V_5$ and $V_6$. The shield of each signal lead 1–10 is connected to one of the rectangular connectors in the lower row (connections consistent with the AAMI standard), which are connected to a floating ground G.

Grounding of the shields of the signal leads has an importance especially in ECG monitoring performed during anesthesia, because surgical operations are often performed using a so-called diathermic device, i.e. an electric surgical knife, whose high-frequency electric current would otherwise confuse the ECG monitoring process.

The figure also shows protective resistors 23, whose function is to protect the amplifier electronics against the high-voltage pulse of a defibrillator. Two resistors are provided for each one of leads 1–5 because in most cases, in addition to ECG measurement, the patient's respiration also needs to be monitored, which is done using a parallel apparatus measuring thorax impedance.

The problem with the prior-art system is that, in a 12-lead system, the collecting adapter is a very wide, large and heavy component when traditional, standardized shielded signal leads are used, in which each conductor runs inside a separate shield. The large size and weight are a problem in respect of usability, because the aforesaid collecting adapter is usually placed near the patient and can easily be dropped to the floor, where the adapter and the leads connected to it may be damaged.

The object of the invention is to eliminate the problems referred to above.

A specific object of the invention is to disclose a system which can work both as a 5-lead system and as a 12-lead system and in which it is possible to combine a 5-lead and a 12-lead amplifier connector and signal leads, allowing the same amplifier unit to function alternatively in a 5-lead system with shielded leads or in a 12-lead system with unshielded leads.

A further object of the invention is to disclose a system in which a small and light-weight collecting adapter can be used.

As for the features characteristic of the invention, reference is made to the claims presented below.

According to the invention the system comprises measuring attached to a patient in accordance with a standard electrode placement; signal leads connected to corresponding measuring electrodes each of said signal leads being provided with a first connector element; a collecting connector containing second connector elements for receiving the first connector elements; an ECG apparatus comprising an amplifier unit to which the measurement signals are passed from the collecting connector; and change-over switches which are so implemented that, in a first connection position, they will conduct the measurement signals from the measuring electrodes attached to the patient to the ECG apparatus so that the corresponding signal leads are electrically connected to the patient, while in a second connection position they establish a shielding ground connection for at least some of said signal leads.

Shielding is not necessarily needed in all monitoring situations, so it is possible to use signal leads substantially without a shielding ground connection.

In an embodiment of the system, the collecting connector is placed in the amplifier unit, and the signal leads are connected directly from the patient to the amplifier unit.

In an embodiment of the system, the system comprises a collecting cable between the signal leads and the amplifier unit. In this case, the collecting connector is connected to the collecting cable.

In an embodiment of the system, the collecting connector comprises a number of second connector elements corresponding to the number of measuring electrodes defined in the 12-lead ECG standard.

In an embodiment of the system, the changeover switches in their second connection position establish a shielding ground connection for a first group of signal leads via the connector elements in the collecting connector intended for a second group of signal leads In an embodiment of the system, the measuring electrodes are connected to the patient in accordance with the 12-lead ECG standard. In this case, in order to accomplish a 12-lead ECG measurement, the changeover switches are in the said first position to pass the measurement signals from all measuring electrodes to signal processing in the ECG apparatus the signal leads now being electrically connected to the patient.

In an embodiment of the system, the measuring electrodes are connected to the patient in accordance with the 5-lead ECG standard. In this case, to accomplish a 5-lead ECG measurement with grounded shielding, the change-over switches are in the said second position, the first group of signal leads now having a shielding ground connection to a floating ground.

In an embodiment of the system, the second connector elements in the collecting connector are arranged in two adjacent rows, where the second connector elements in one row are disposed in paired alignment with the connector elements in the other row.

In an embodiment of the system, the changeover switches are disposed in the amplifier unit.

In an embodiment of the system, the changeover switches are controllable analog switches.

In an embodiment of the system, the system comprises a control device for the control of the change-over switches.

In an embodiment of the system, the control device comprises means allowing the change-over switches to be controlled by the user.

In an embodiment of the system, the control device comprises detection means so implemented that they will automatically detect the connection state (lead on/lead off) of a measuring electrode to a patient; and means for selecting the connection position of the change-over switches from between said first connection position and said second connection position on the basis of said automatic detection.

In an embodiment of the system, the detection means are so implemented that they will automatically detect convection of the measuring electrodes to a patient by measuring the resistance of the measuring electrodes.

In an embodiment of the system, the signal leads comprise a set of standard precordial leads and a set of standard limb leads.

In an embodiment of the system, the connection elements for the limb leads and for one precordial lead are arranged in the first row in the collecting connector, and the connection elements for the rest of the precordial leads are arranged in the second row in the collecting connector the second row being in paired alignment with said first row.

In an embodiment of the system one of the limb leads is defined to be unshielded in both 5-lead and 12-lead measurement mode. The detection means are disposed to continuously monitor the connection state (lead on/lead off) of one precordial lead to determine which of the monitoring modes (5-lead or 12-lead) to be used.

In an embodiment of the system said lead being unshielded and continuously monitored is the precordial lead for which a connecting element is dedicated in the second row of connecting elements at the collecting connector, said connecting element in the second row being in paired alignment with another connecting element in the first row of connecting elements at the collecting connector, said another connecting element in the first row being dedicated f or the Neutral lead from the set of standard limb leads.

In an embodiment of the system, the detection means are so implemented that they will automatically identify the signal lead types used, by measuring the capacitances regardless of whether the leads are connected to a patient or not.

In an embodiment of the system the collecting connector comprises a separate shield connector common for all signal leads.

In an embodiment of the system the collecting connector for a 12-lead cable is mechanically coded, so as not to mare with a standard 5-lead connector.

In the following, the invention will be described in detail by the aid of a few examples of its embodiments with reference to the attached drawing, wherein.

Figure 3:
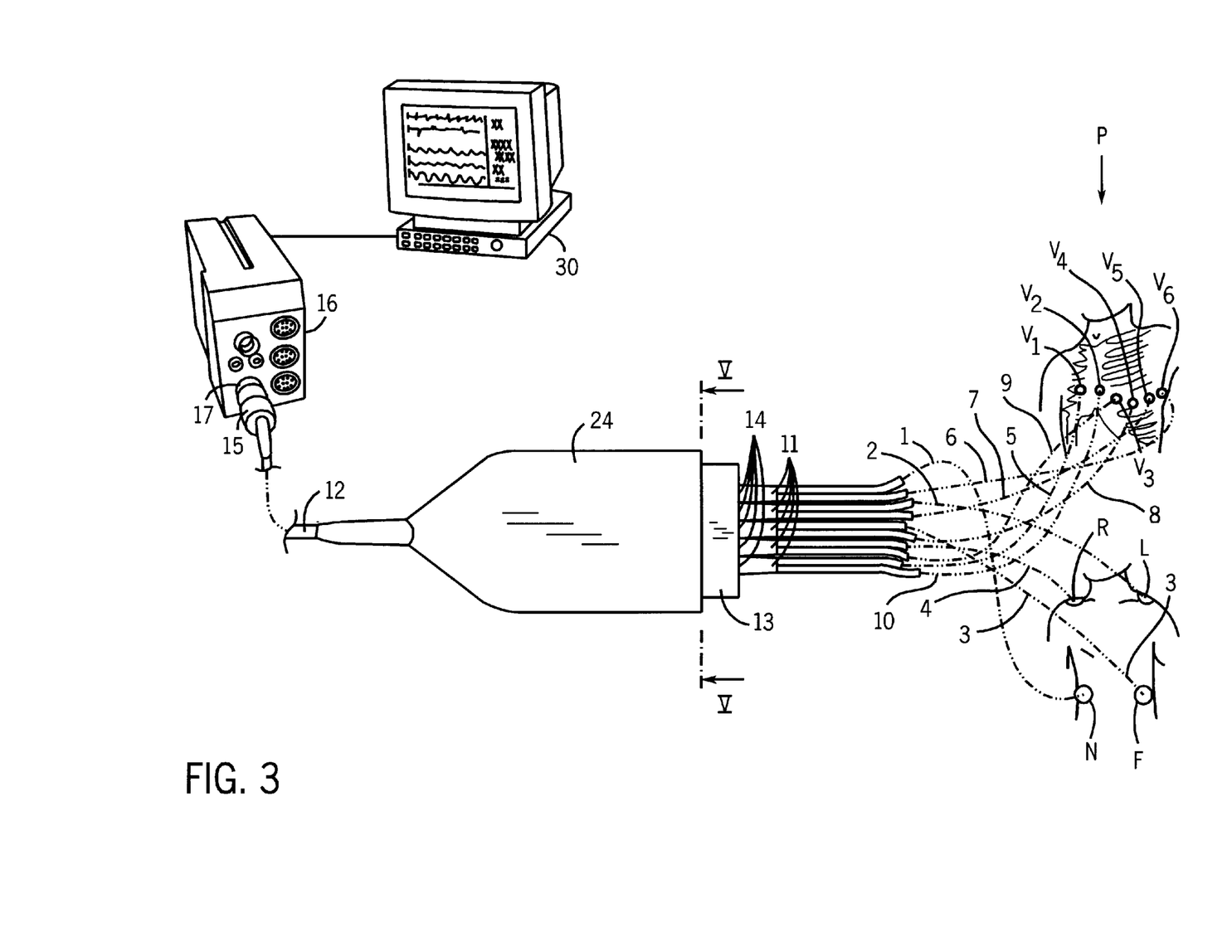
FIG. 3 presents a diagram representing a first embodiment of the system of the invention.

FIG. 3 presents an ECG monitoring system comprising signal leads 1–10, which are connected in accordance with the standard electrode placement to corresponding limb electrodes R, F, L, N and precordial electrodes $V_1$, $V_2$, $V_3$, $V_4$, $V_5$, $V_6$ attached to the patient P. The signal leads comprise a pet of standard precordial leads 5–10 for precordial electrodes $V_1$, $V_2$, $V_3$, $V_4$, $V_5$, $V_6$ and a set of standard limb leads 1–4 for the limb electrodes R, F, L, N.

Each signal lead 1–10 is provided with a first connector element 11. One end of the collecting cable 12 is provided with an adapter 24 comprising a collecting connector 13. The collecting connector 13 contains second connector elements 14, to which the first connector elements 11 of the signal leads are connected. The other end of the collecting cable 12 is provided with a third connector element 15. The ECG apparatus comprises an amplifier unit 16, which is provided with a fourth connector element 17, to which the third connector element 15 is connected.

Figure 4:
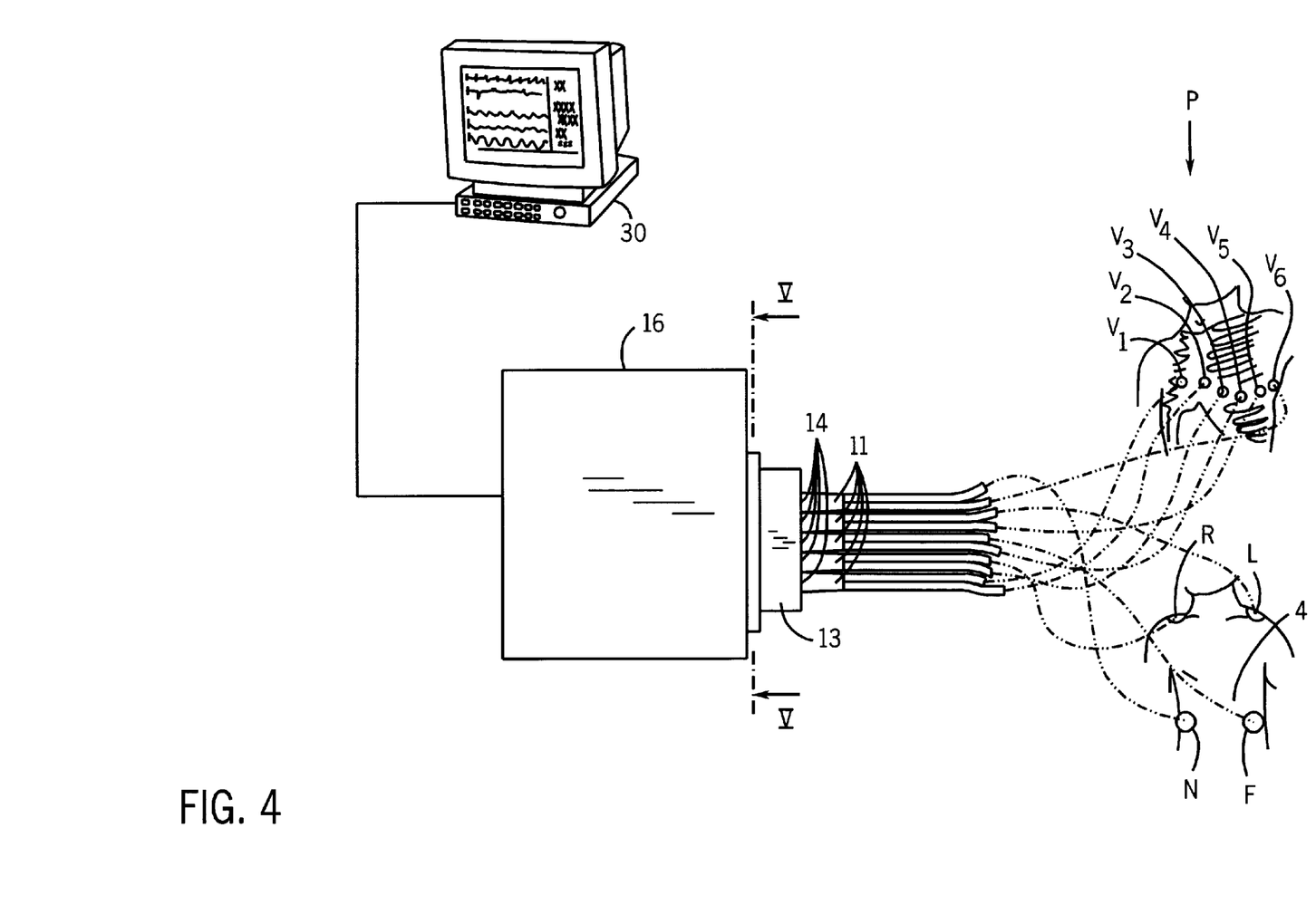
FIG. 4 presents a diagram representing a second embodiment of the system of the invention.

FIG. 4 presents a second preferred embodiment of the system, which corresponds to the embodiment in FIG. 3 except that no collecting cable is used at all; instead, the signal leads 1–10 are taken directly from the patient P to the amplifier unit 16, which is provided with a collecting connector 13. The collecting connector 13 is of a kind corresponding to the collecting connector at the end of the collecting cable in the embodiment in FIG. 3. In the following, the connector and the connections in it will be described in detail with reference to FIG. 5.

Figure 5:
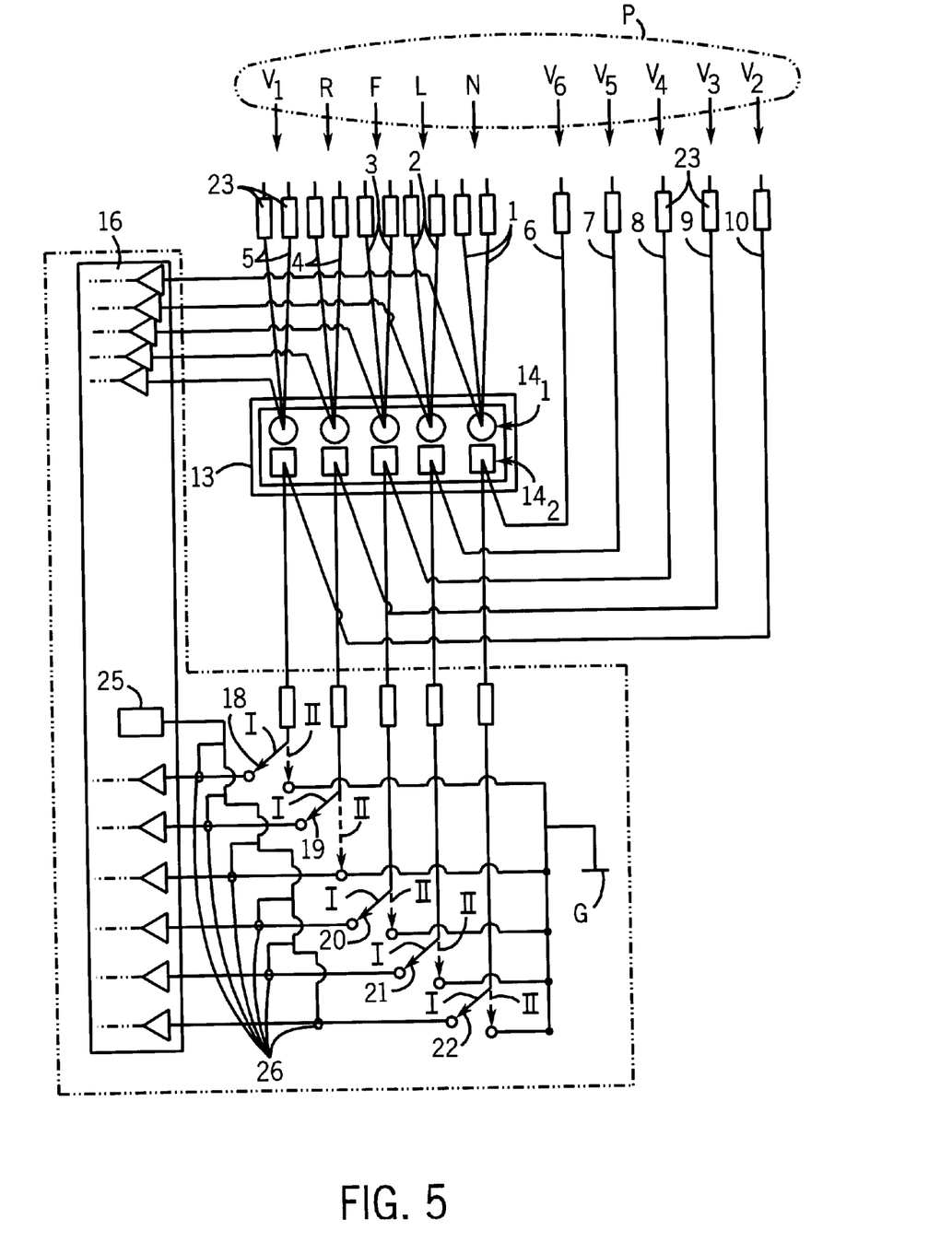
FIG. 5 presents a diagram representing a collecting connector as seen from direction V—V in FIGS. 3 or 4, as well as a diagram of the system.

As shown in FIG. 5, the collecting connector 13 in the embodiments presented in FIGS. 3 and 4 contains a number of second connector elements 14; $14_1$, $14_2$ corresponding to the number of measuring electrodes defined in the 12-lead ECG standard, i.e. a total of 10 connector elements. As can be seen, the connection elements for the limb leads 1–4 connected to the limb electrodes R, F, L, N and for one precordial lead 5 of the precordial electrode $V_1$ are arranged in the upper first row $14_1$ in the collecting connector 13. The connection elements for the rest of the precordial leads 6–10 connected to the rest of the precordial electrodes $V_2$, $V_3$, $V_4$, $V_5$, $V_6$ are arranged in the lower second row $14_3$ in the collecting connector 13 the second row $14_2$ being in paired alignment with said first row.

The electronics of the amplifier unit 16 is provided with analog change-over switches 18–22 controllable by the microprocessor of the ECG apparatus 30. The change-over switches have two connection positions I and II. In the first connection position I, the measurement signals are passed from all the measuring electrodes R, F, L, N; $V_1$, $V_2$, $V_3$, $V_4$, $V_5$, $V_6$ connected to the patient P to the ECG apparatus in such manner that the corresponding signal leads 1–10 are connected to the patient. In the second connection position II (depicted with a broken line in FIG. 5), the change-over switches 18–22 have been turned to a position in which they establish a shielding ground connection to a so-called floating ground G for certain signal leads. In the second connection position II, the change-over switches 18–22 establish a shielding ground connection for the first group 1–5 of signal leads via the second connector elements $14_2$ in the collecting connector 13 intended for the second group 6–10 of signal leads.

Both in 5-lead and in 12-lead ECG monitoring modes can be used a collecting connector which resembles a conventional existing collecting connector designed for a 5-lead system, which means in practice that the shield connections $14_2$ of the 5-lead system are utilized by the precordial electrodes $V_2$, $V_3$, $V_4$, $V_5$, $V_6$ of the 12-lead system. In the 12-lead measuring mode, the existing signal leads are used without shielding earth connections, whereas in the 5-lead measuring mode the existing signal leads are used with shielding earth connections. The required essential change is the provision of change-over switches 18–22 in the electronics of the amplifier unit 16.

In FIG. 5, the change-over switches 18–22 are in position I, depicted with a solid line, to allow a 12-lead ECG measurement to be carried out. The limb electrodes R, F, L, N and the precordial electrodes $V_1$, $V_2$, $V_3$, $V_4$, $V_5$, $V_6$ are connected to the patient in accordance with the 12-lead ECG standard. The measurement signals are conducted by signal leads 1–10 without a shielding ground connection via all ten connector elements $14_1$ and $14_2$ in the collecting connector 13 to the amplifier unit 16 and further in a conventional manner to a signal processing stage in the ECG apparatus.

Alternatively, when the change-over switches 18–22 are in position II, depicted with a broken line in FIG. 5, the measurement signals are conducted from the measuring electrodes R, L, N, F, $V_1$ placed on the patient in accordance with the 5-lead ECG standard via the five second connector elements $14_1$ in the upper row of signal leads 1–5 in the collecting connector 13 to the amplifier unit 16 and further in a conventional manner to a signal processing stage in the ECG apparatus, and the signal leads 1–5 are shielded by a floating ground through the second connector elements $14_2$ in the lower row as these are now connected via the change-over switches 18–22 to a floating ground G. In this case, the second group 6–10 of signal leads may be simultaneously connected to the connector elements $14_2$ in the lower row or not; in any case, no signals are now passed through them to the amplifier or to the ECG apparatus.

The second connector elements $14_1$ and $14_2$ have been arranged in the collecting connector 13 in two adjacent rows, in which the second connector elements $14_1$ and $14_{,2}$ are in alignment with each ocher.

The system preferably comprises a control device 25, e.g. software means provided in the microprocessor of the ECG apparatus, for the control of the change-over switches 18–22 The change-over switches 18–22 may either be controllable by the user or they may be controlled by an automatic system. The control device 25 may also comprise detection means 26 for automatically detecting whether the measuring electrodes are connected to a patient or not. The connection position I or II of the change-over switches 18–22 can then be selected on the basis of this detection. The automatic system may also be so implemented that it will detect connection of the measuring electrodes to a patient by measuring the resistance of the measuring electrodes, and that, it the resistance is lower than a predetermined limit value, it will detect a disconnected state of the electrode (conventional 'leads-off' detection using a high-resistance pull-up resistor). A more accurate detection of the disconnected state for the selection of an ECG measuring mode can be accomplished by measuring the capacitance exceeding a limit value between the shield and the core of the signal lead, in which case detection will be possible regardless of whether the leads are connected to a patient or not.

Figure 6:
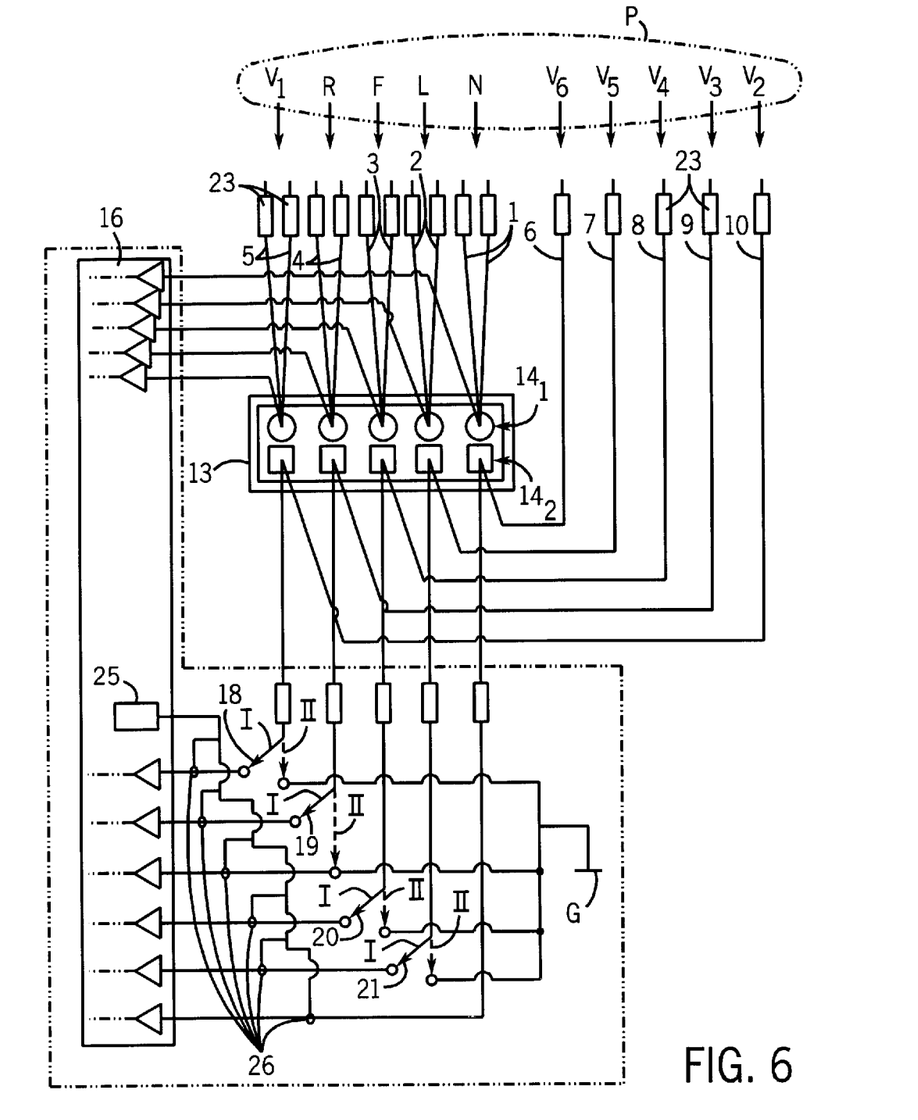
FIG. 6 presents a further embodiment of the system presented in analogous manner as in FIG. 5, and FIG. 7. shows an end view of a mechanically coded collecting connector.

FIG. 6 shows a further development of the system which differs from the system of FIG. 5 in that one of the limb leads, namely limb lead 1 is defined to be unshielded in both 5-lead and 12-lead measurement modes. The detection means are disposed to continuously monitor the connection state (lead on/lead off) of one precordial lead 6 of one precordial electrode $V_6$ to determine which of the monitoring modes (5-lead or 12-lead) to be used. The precordial lead 6 is connected to the precordial electrode $V_5$ for which there is a connecting element dedicated in the second row $14_2$ of connecting elements at the collecting connector 13. This connecting element for the precordial lead 6 is in paired alignment with another connecting element in the first row $14_1$ at the collecting connector 13. This another connecting element in the first row $14_1$ is dedicated for the Neutral lead 1 of the Neutral limb electrode N from the set of standard limb leads R, F, L, N. The Neutral lead 1 of the Neutral limb electrode is an output and, thus, leaving it unshielded (as can be seen from FIG. 6, there is no need for a changeover switch for the precordial lead $V_6$) does not affect the common mode rejection ratio (CMRR) of the amplifier. Therefore, the lead resistance of the precordial lead $V_6$ connected to the Neutral lead N can be constantly monitored to determine the connection state (lead on/lead off) thus allowing a smooth transition between 5 and 12 lead monitoring modes. If the resistance is low, then the connection state is "lead on". If the resistance is high, then the connection state is "lead off". If all precordial leads are in the connection state "lead off" then the monitoring mode is switched to the 5-lead monitoring mode. The monitoring of the connection state of the constantly unshielded precordial lead 6 for $V_6$ is continued. If "lead on" is detected then the monitoring mode is switched to the 12-lead monitoring mode. Continuous checking of the precordial lead 6 for $V_6$ guarantees a correct cable configuration as soon as the precordial lead 6 for $V_6$ is connected, even if the previous mode was the 5-lead mode with all other precordial leads connected to ground. The advantage is the ability to be AAMI compatible (shields connected to ground) with the 5-lead cable, and also be able to use the square connectors in the lower second row 14₂ for precordial leads when the 12-lead monitoring cable is connected.

Figure 7:
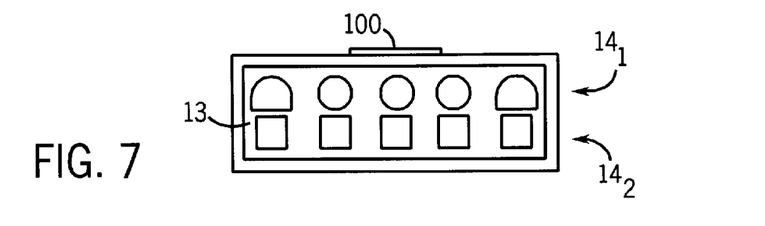

FIG. 7 shows a collecting connector 13 for a 12-lead lead set, according to the present invention. It is provided with a separate common shield connector 100 which is common for all signal leads 1–10, The collecting connector 13 is also mechanically coded, so as not to mate with a standard 5-lead connector. The mechanical coding is implemented by reshaping two of the connector holes in the first row 14₁ of the female connector. The 12-lead male connector has similarly shaped male connectors in the first row 14₁. Therefore the 12-lead male connector with said two reshaped male connectors does not mate with a standard 5-lead female connector with five round connector holes in the first row. However, the female connector as shown in FIG. 7 is able to mate both with a standard 5-lead male connector with five round male connectors and with a new 12 lead male connector with three round and two reshaped male connectors.

The invention is not restricted to the examples of its embodiments described above; instead, many variations are possible within the scope of the inventive idea defined in the claims.

What is claimed is:

1. System for ECG monitoring, comprising
   measuring electrodes (R, F, L, L, N; $V_1$, $V_2$, $V_3$, $V_4$, $V_5$, $V_6$) attached to a patient (P) in accordance with a standard electrode placement,
   signal leads (1–10) connected to corresponding measuring electrodes (R, F, L, N; $V_1$, $V_2$, $V_3$, $V_4$, $V_5$, $V_6$) each of said signal leads being provided with a first connector element (11),
   a collecting connector (13) containing Second connector elements (34) for receiving the first connector elements (11),
   an ECG apparatus comprising an amplifier unit (16) to which the measurement signals are passed from the collecting connector, and
   change-over switches (18–22) which are so implemented that, in a first connection position (I), they will conduct the measurement signals from the measuring electrodes (R, F, L, N; $V_1$, $V_2$, $V_3$, $V_4$, $V_5$, $V_6$) attached to the patient (P) to the ECG apparatus so that the corresponding signal leads (1–10) are electrically connected to the patient, while in a second connection position (II) they establish a shielding ground connection for at least some of said signal leads.

2. System as defined in claim 1 wherein the system comprises a collecting cable (12) between the signal leads (1–10) and the amplifier unit (16); and that the collecting connector (13) is connected to the collecting cable.

3. System as defined in claim 1 wherein the collecting connector (13) is placed in the amplifier unit (16), in which case the signal leads (1–10) are passed directly from the patient to the amplifier unit.

4. System as defined in claim 1 wherein the collecting connector (13) has a number of second connector elements (14₁, 14₃) corresponding to the number of electrodes defined in the 12-lead ECG standard.

5. System as defined in claim 1 wherein the change-over switches (18–22) in their second, connection position (II) establish a shielding ground connection for a first group of signal leads (1–5) via the connector elements (14₂) in the collecting connector (13) intended for a second group of signal leads (6–10).

6. System as defined in claim 1 wherein the measuring electrodes (R, L, N, F; $V_1$, $V_2$, $V_3$, $V_4$, $V_5$, $V_6$) are connected to the patient in accordance with the 12-lead ECG standard, and that, to accomplish a 12-lead ECG measurement, the change-over switches (18–22) are in the said first position (I) to pass the measurement signals from all the measuring electrodes to signal processing in the ECG apparatus.

7. System as defined in claim 1 wherein the measuring electrodes (R, L, N, F, $V_5$) are connected to the patient in accordance with the 5-lead ECG standard, and that, to accomplish a 5-lead ECG measurement with grounded shielding, the change-over switches (18–22) are in the said second position (II), the first group of signal leads (1–5) now having a shielding ground connection lo a floating ground.

8. System as defined in claim 1 wherein the second connector elements (14) in the collecting connector (13) are arranged in two adjacent rows, where the second connector elements (14₁) in one row are disposed in paired alignment with the connector elements (14₂) in the other row.

9. System as defined in claim 1, characterized in that the change-over switches (18–22) are disposed in the amplifier unit (16).

10. System as defined in claim 1 wherein the change-over switches (18–22) are controllable analog switches.

11. System as defined in claim 1 wherein the system comprises a control device (25) for the control of the change-over switches (18–22).

12. System as defined in claim 11 wherein the control device comprises means allowing the changeover switches (18–22) to be controlled by the user.

13. System as defined in claim 11 wherein the control device comprises detection means (26) so implemented that they will automatically detect the connection state (lead on/lead off) of a measuring electrode to a patient; and means for selecting the connection position of the change overswitches (18–22) from between the first connection position (I) and the second connection position (II) on the basis of said automatic detection of the connection state of the measuring electrode.

14. System as defined in claim 13 wherein the detection means (25) are so implemented that they will automatically detect the connection state (lead on/lead off) of the measuring electrodes to a patient by measuring the resistance of the measuring electrodes.

15. System as defined in claim 1 wherein the signal leads comprise a set of standard precordial leads ($V_1$, $V_2$, $V_3$, $V_4$, $V_5$, $V_6$) and a set of standard limb leads (R, F, L, N).

16. System as defined in claim 15 wherein the connection elements for the limb leads (1–4) connected to the lit electrodes (R, F, L, N), and for one precordial lead (5) of one precordial electrode ($V_1$) are arranged in the first row (14₁) in the collecting connector (13), and the connection elements for the rest of the precordial leads (6–10) connected to the rest of the precordial electrodes ($V_2$, $V_3$, $V_4$, $V_5$, $V_6$) are arranged in the second row (14₂) in the collecting connector (13) the second row being in paired alignment with said first row.

17. System as defined in claim 16 wherein one of the limb leads (N) is defined to be unshielded in both 5-lead and 12-lead measurement mode; and that the detection means are disposed to continuously monitor the connection state (lead on/lead off) of one precordial lead (6) of one precordial electrode ($V_6$) to determine which of the monitoring modes (5-lead or 12-lead) to be used.

18. System as defined in claim 17 wherein said lead being unshielded and continuously monitored is the precordial lead connected to a precordial electrode ($V_6$) for which a connecting element is dedicated in the second row (14$_2$) of connecting elements at the collecting connector (13), said connecting element in the second row being in paired alignment with another connecting element in the first row (14$_1$) of connecting elements at the collecting connector (13), said another connecting element in the first row being dedicated for the Neutral lead (1) from the set of standard list leads (R, F, L, N).

19. System as defined in claim 13 wherein the detection means are so implemented that they will automatically identify the signal lead types used, by measuring the capacitances regardless of whether the leads are connected to a patient or not.

20. System as defined in claim 1 wherein the collecting connector comprises a separate common shield connector (100) which is common for all signal leads.

21. System as defined in claim 1 wherein the collecting connector for a 12-lead cable is mechanically coded, so as not to mate with a standard 5-lead connector.

22. System for ECG monitoring, comprising measuring electrodes (R, F, L, N; $V_1$, $V_2$, $V_3$, $V_4$, $V_5$, $V_6$) attached to a patient (P) in accordance with a standard electrode placement, signal leads (1–10) connected to corresponding measuring electrodes (R, F, L, N; $V_1$, $V_2$, $V_3$, $V_4$, $V_5$, $V_6$) each of said signal leads being provided with a first connector element (11), a collecting connector (13) containing second connector elements (14) for receiving the first connector elements (11), an ECG apparatus comprising an amplifier unit (16) to which the measurement signals are passed from the collecting connector, and change-over switches (18–22) which are so implemented that, in a first connection position (I), they will conduct the measurement signals from the measuring electrodes (R, F, L, N; $V_1$, $V_2$, $V_3$, $V_4$, $V_5$, $V_6$) attached to the patient (P) to the ECG apparatus so that the corresponding signal leads (1–10) have no shielding ground connection, while in a second connection position (II) they establish a shielding ground connection for at least some of said signal leads.

\* \* \* \* \*